US010368530B2

(12) United States Patent
Bolen

(10) Patent No.: US 10,368,530 B2
(45) Date of Patent: Aug. 6, 2019

(54) METHOD, SYSTEM, AND APPARATUS FOR DETERMINING LOCATION OF ANIMALS IN COMPETITIVE ENVIRONMENTS

(71) Applicant: Lip Chip LLC, Austin, TX (US)

(72) Inventor: Bradley Bolen, San Angelo, TX (US)

(73) Assignee: Lip Chip, LLC, Austin, TX (US)

( * ) Notice: Subject to any disclaimer, the term of this patent is extended or adjusted under 35 U.S.C. 154(b) by 17 days.

(21) Appl. No.: 15/827,487

(22) Filed: Nov. 30, 2017

(65) Prior Publication Data
US 2019/0159428 A1    May 30, 2019

(51) Int. Cl.
*A63F 9/24* (2006.01)
*A01K 11/00* (2006.01)
*A01K 29/00* (2006.01)
*G01S 1/00* (2006.01)
*G07C 1/24* (2006.01)
*G01K 1/02* (2006.01)

(52) U.S. Cl.
CPC .......... *A01K 11/008* (2013.01); *A01K 29/005* (2013.01); *G01S 1/00* (2013.01); *A61B 2503/40* (2013.01); *A63B 2220/80* (2013.01); *G01K 1/024* (2013.01); *G07C 1/24* (2013.01)

(58) Field of Classification Search
CPC ...... G07F 17/32; G07F 17/3288; H04W 4/02; G01S 5/0009; G01S 1/08
See application file for complete search history.

(56) References Cited

U.S. PATENT DOCUMENTS

| 6,910,050 | B2 | 6/2005 | Pawlick | |
|---|---|---|---|---|
| 7,589,638 | B2 | 9/2009 | Jackson | |
| 9,717,216 | B1 | 8/2017 | Schlachta | |
| 2008/0052178 | A1* | 2/2008 | Yamashita | G06Q 20/00 705/24 |
| 2008/0139316 | A1* | 6/2008 | He | G06Q 10/00 463/42 |
| 2016/0133086 | A1* | 5/2016 | Al Kuwari | G07F 17/3204 463/6 |
| 2016/0364689 | A1* | 12/2016 | Terry | G06Q 10/0833 |
| 2017/0006838 | A1* | 1/2017 | Brayer | A01J 5/007 |

* cited by examiner

*Primary Examiner* — Hongmin Fan
(74) *Attorney, Agent, or Firm* — Cullen Kiker; Orgain Bell & Tucker LLP

(57) ABSTRACT

A tag is implanted in the forwardmost part of an animal to determine the location of the animal for competitive and security purposes. The tag is implanted such that it is inserted in the first part of an animal to cross a finish line. By using the tag to determine the when an animal has reached a predetermined location, the method and system can evaluate the results of the race, negating the need for human judgment. Further, the invention allows for tracking of the animal in transit and when at a race grounds.

15 Claims, 14 Drawing Sheets

METHOD, SYSTEM, AND APPARATUS FOR DETERMINING LOCATION OF ANIMALS IN COMPETITIVE ENVIRONMENTS

BACKGROUND

Winners in competitive races, such as horse racing, are determined by when the forwardmost part of the racing animal passes the finish line. While some races can easily be decided by a simple visual observation, other races involve animals crossing the fish line at almost the same time, requiring a more accurate means to determine which animal did in fact cross the finish line first.

Another issue related to racing animals involves monitoring when animals have entered or exited a certain area. When animals enter a racing facility there are various locations where they must pass in order to get where then need to be. For example, animals entering the race grounds, entering the stables, entering the raceway, and entering the post all need be monitored.

An additional issue in racing competitions involves proper identification of the animals. Prior identification methods involved the use of tattoos that fade over time. A more recent practice involved having a tag implanted in the animal that may be interrogated by a device that can read the tag to identify the animal. However, these tags have a limited functionality, such as basic record keeping and generalized location determination.

An additional issue with racing animals is the need to have specific paperwork showing the animal complies with regulations before a race, such as proper immunizations. Owners routinely provide such paperwork at the initial check in when the animal enters the race grounds. This can lead to a considerable delay as a line may form at the race grounds entrance as people get their papers inspected. Additionally, in the event paperwork is not available, owners have been known to change the paperwork to let an otherwise ineligible horse enter the race.

BRIEF SUMMARY OF INVENTION

A method of the disclosed invention in an exemplary embodiment comprises implanting a tag in the lip of an animal and receiving of that signal to determine the location of the animal. By placing the tag in the lip of an animal, the tag will be in the forward most part of the animal when it is running. This allows the tag to be used to determine which animal of a plurality of animals reaches a finish line first. In addition to determining the animal's location, it may also contain information to facilitate services associated with racing, such as locating the animal and providing documentation.

A system of the disclosed invention in an exemplary embodiment comprises a tag implanted in the forward part of an animal that can send information to a reader in such a manner that the location of the animal may be known. By receiving the location of multiple animals in a competitive racing environment, the winner of a race may be determined.

BRIEF DESCRIPTIONS OF FIGURES

DETAILED DESCRIPTION

The present invention provides information on an animal. While this may be adapted to any animal, exemplary embodiments will refer to horses 102.

The tag 100 is an implantable device sized to easily be inserted into the horse 102 near the surface. The tag 100 allows for multiple functions that may be expanded upon below. These features may include use in competitions, animal tracking, and record keeping. The tag 100 will contain multiple elements. Possible elements include a transmitter, a receiver, a power supply, memory, and a processor depending on the embodiment. Some or all of these elements may be included in various configurations without departing from the scope of the invention.

Figure 1A:
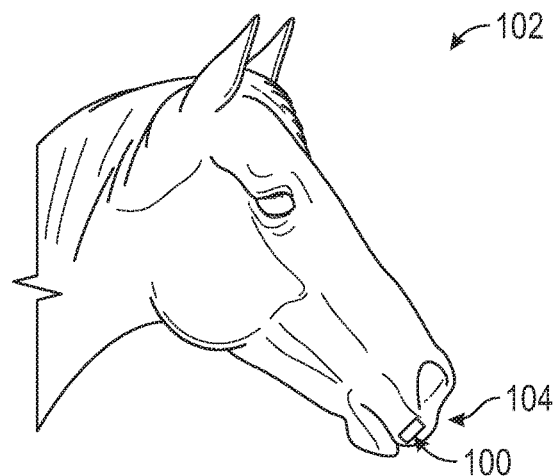
FIG. 1A shows the location of a tag in the lip of a horse in an exemplary embodiment.
Figure 1B:
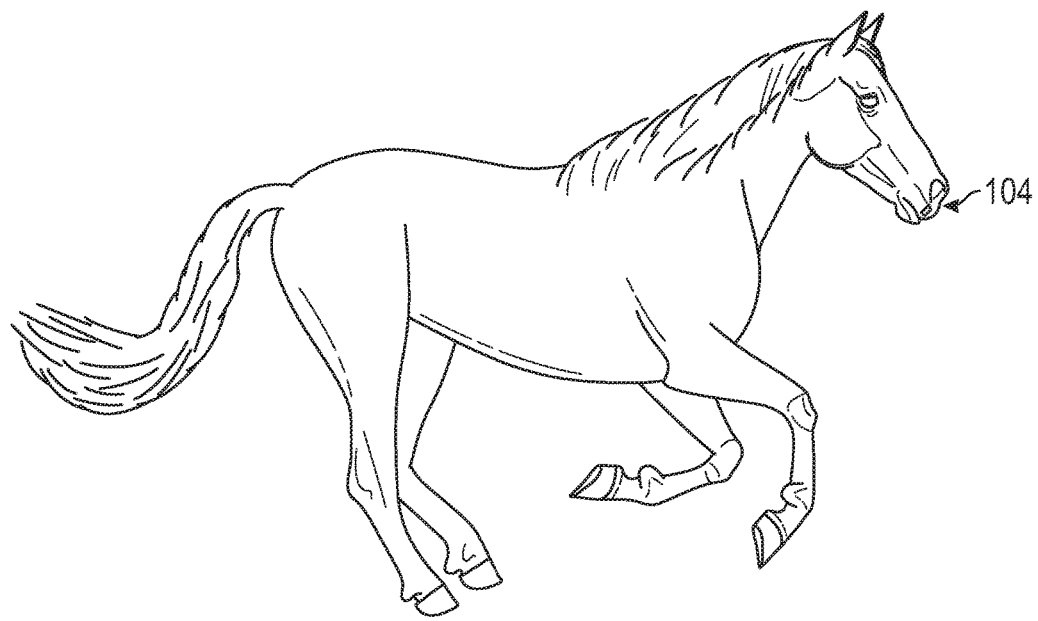
FIG. 1B illustrate a horse running, showing how the lip is the forwardmost part of the horse when running.
Figure 1C:
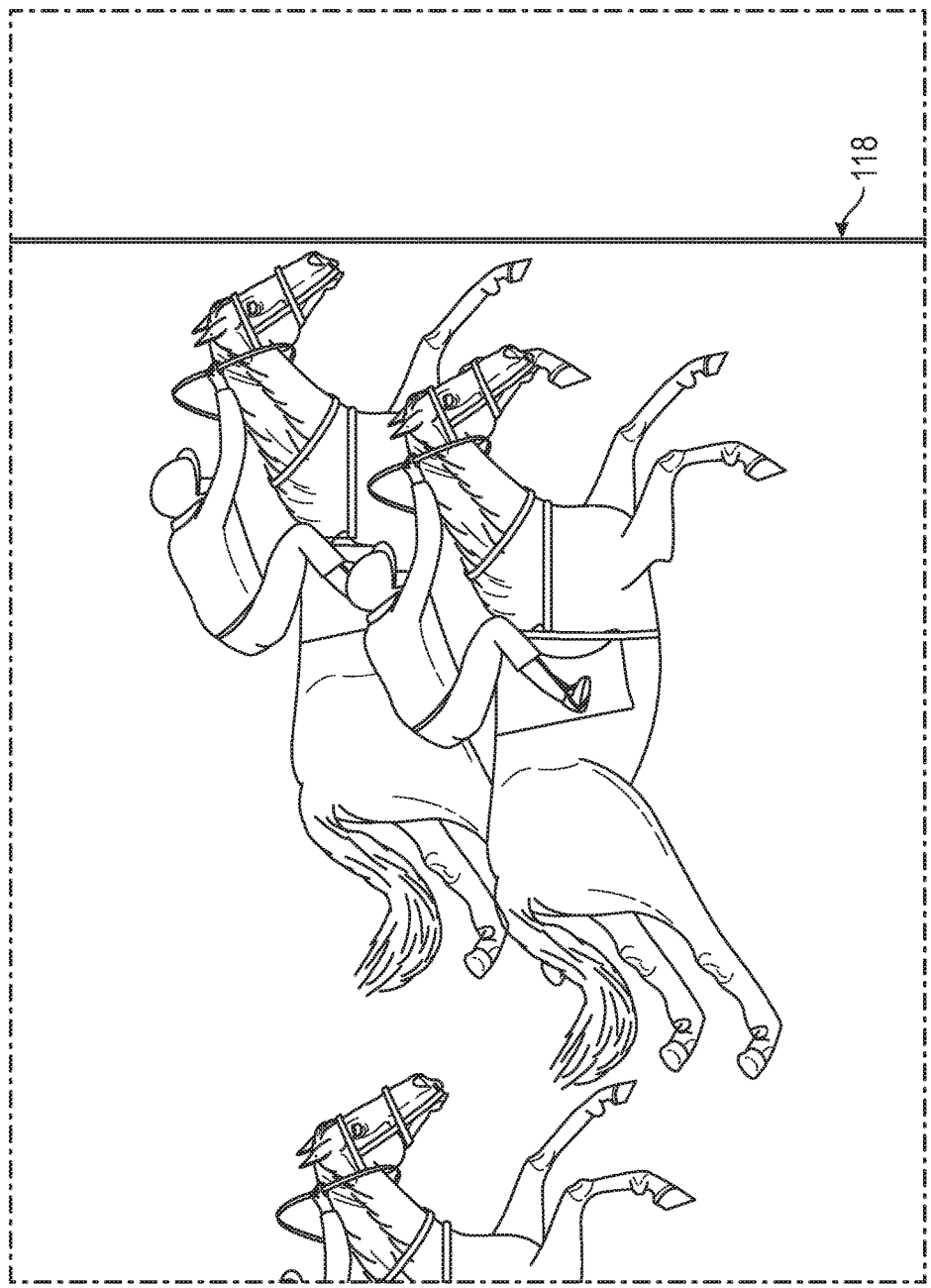
FIG. 1C is an illustration of how the forwardmost part of an animal can determine the winner of a race.

While the tag 100 may be implanted anywhere in the horse 102, there is an advantage in placing it in the lip 104 as shown in FIG. 1A. By placing the tag 100 in the lip 104, the tag 100 will be at the leading edge of the horse 102 at all times. Given the mechanics of a horse 102 when running, the lip 104 area is generally the forwardmost part of the horse 102 when it is running, as shown in FIG. 1B. With the tag 100 installed in the lip 104, the tag 100 will be in approximately the same position in any horse 102 in a race. By the tag 100 being in the most forward part of the horse 102, there would be a standard to determine which horse 102 crossed the finish line 118 first as shown in FIG. 1C, even in the absence of human observation.

Figure 1D:
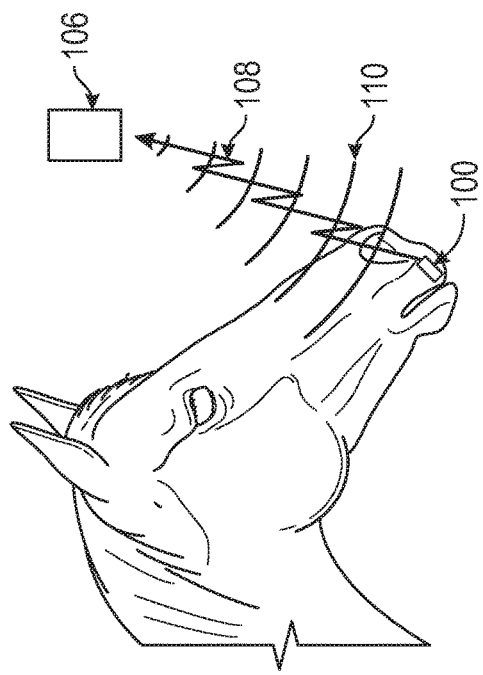
FIG. 1D is an exemplary embodiment of an active transmitter embodiment.
Figure 1E:
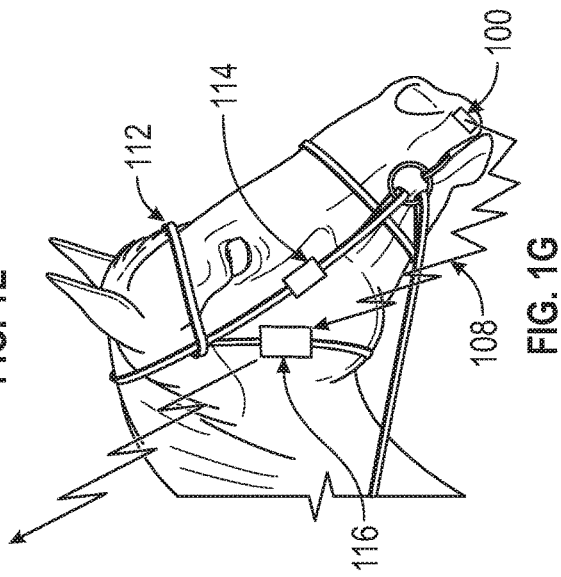
FIG. 1E is an exemplary embodiment of a passive transmitter embodiment.
Figure 5A:
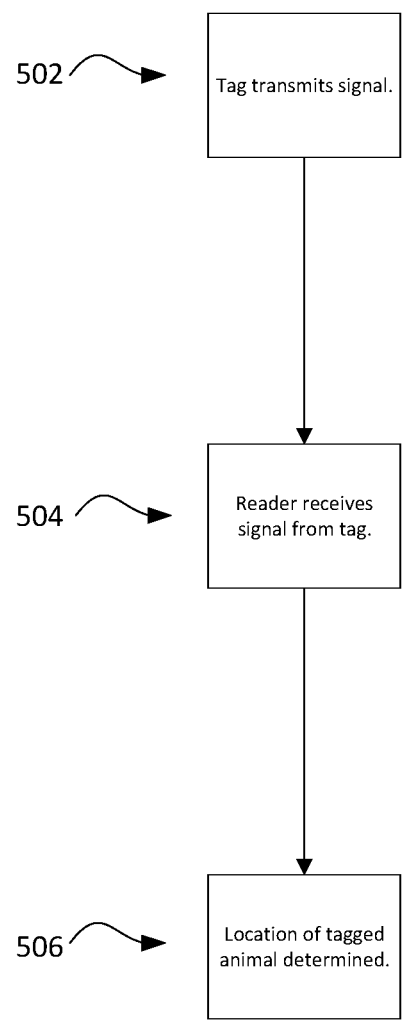
FIG. 5A is a flowchart of an exemplary embodiment showing simplified method of the invention.
Figure 5B:
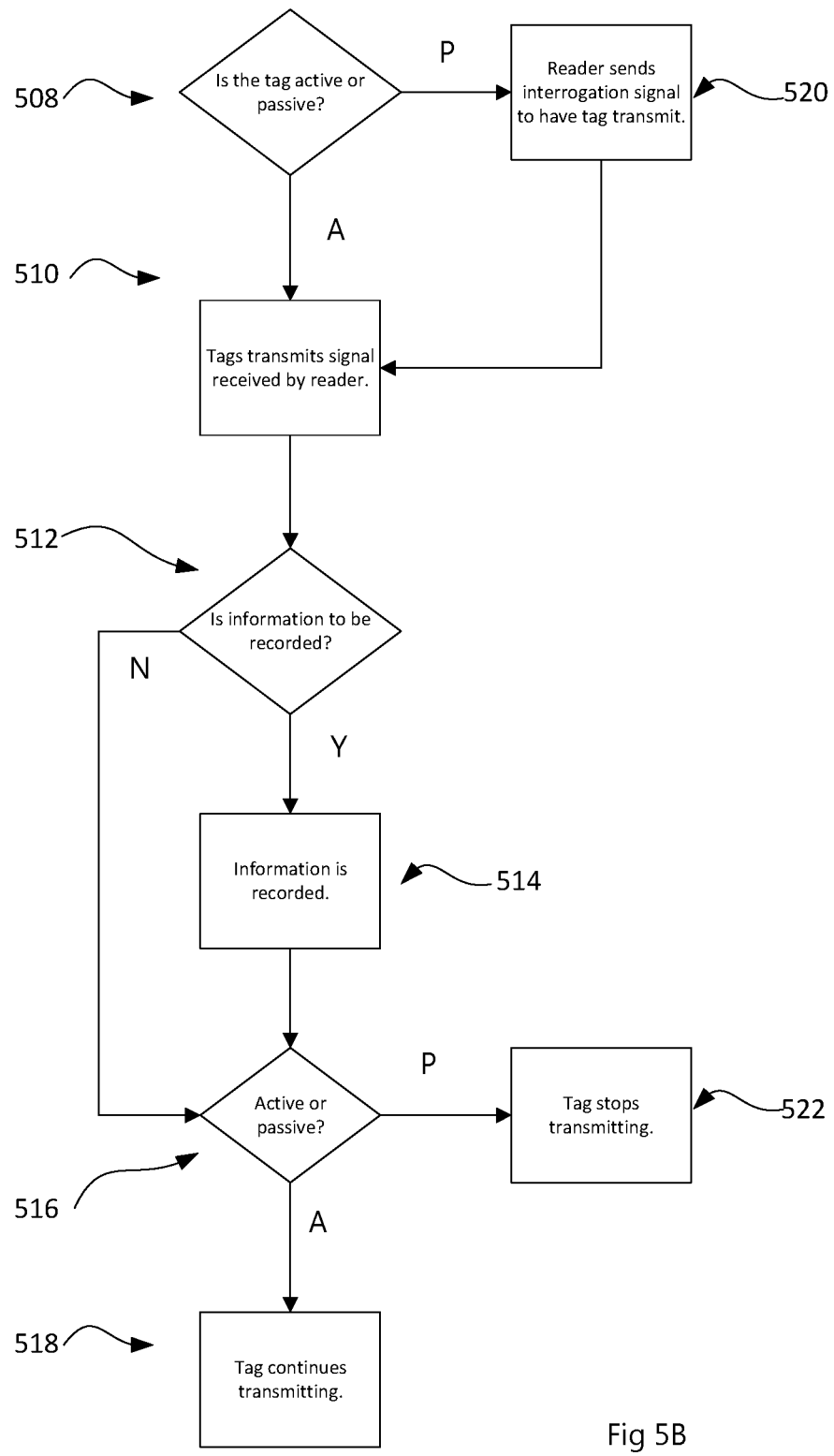
FIG. 5B is a flowchart of an exemplary embodiment showing the difference between active and passive systems.

The tag 100 allows a user to track the location of the horse 102. As shown in FIG. 5A, the tag 100 transmits a signal 108 (step 502), which is received by the reader 106 (step 504). Once the reader 106 receives the signal 108, the location of the horse 102 is known by any means known to those skilled in the art (step 506). FIGS. 1D-E and 5B shows the difference between two different types of tags 100 being active or passive (step 508). If the tag 100 is passive (as in FIG. 1E), the reader 106 sends an interrogation signal 110 (step 520) that causes the tag 100 to transmit a signal 108 read by the reader 106 (step 510). The signal 108 may contain an identification code, location information, or additional information per the specific embodiments. If information is to be recorded (step 512), it is recorded in the memory (step 514). Once the information transfer is complete, the tag 100 will stop transmitting (step 522) in a passive configuration (step 516). If the tag 100 is active (as in FIG. 1D) (step 508), then the tag 100 transmits constantly (step 510, 518), regardless of the presence of a reader 106. In an exemplary embodiment, data will be recorded as needed. Additionally, if there is no information to be received by the reader 106 (step 512), then the information receipt step (step 514) may be bypassed.

Figure 1F:
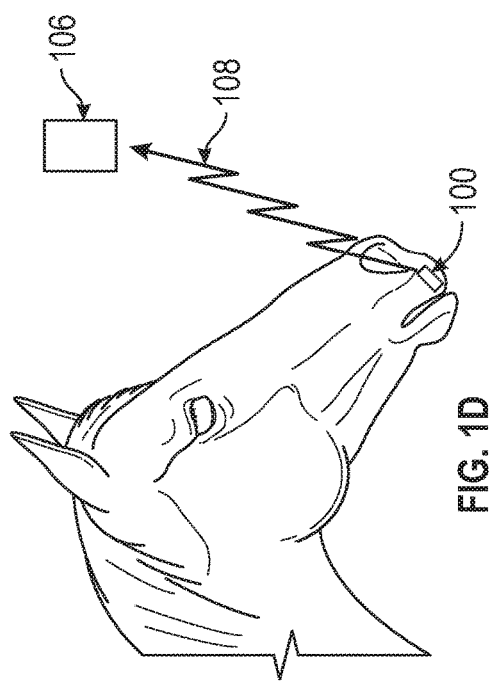
FIG. 1F is an exemplary embodiment of an externally powered embodiment.
Figure 1G:
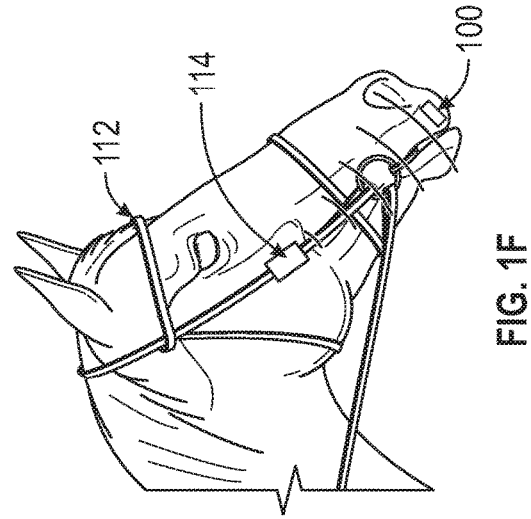
FIG. 1G is an exemplary embodiment of an externally powered embodiment with an additional communications relay.

In the above disclosed embodiments, the tag 100 emits a signal 108 that is detectable by said readers 106. In an exemplary embodiment, the tag 100 may be powered by an internal power supply or receive power from an external source. An internal power supply may be wirelessly powered from a separate external source. The external source may be at a stationary location providing power wirelessly to the tag 100, or it may be mobile. In that embodiment shown in FIG. 1D, the reader 106 is passively receiving the information from the tag 100. In an alternative exemplary embodiment in FIG. 1E, the reader 106 emits an interrogation signal 110 along with wireless energy (such as a magnetic field) which powers the tag 100, causing the tag 100 to transmit a signal 108. In a further additional exemplary embodiment in FIG. 1F, the horse's bridle 112 coupled to the horse 102 might contain a power supply 114 collocated to the tag 100 capable of wirelessly powering the tag 100 via a magnetic field or other means know to those skilled in the art. In FIG. 1G, the bridle 112 may also contain a bridle communications relay 116 that can take the signal 108 and relay it to a secondary location.

Figure 2A:
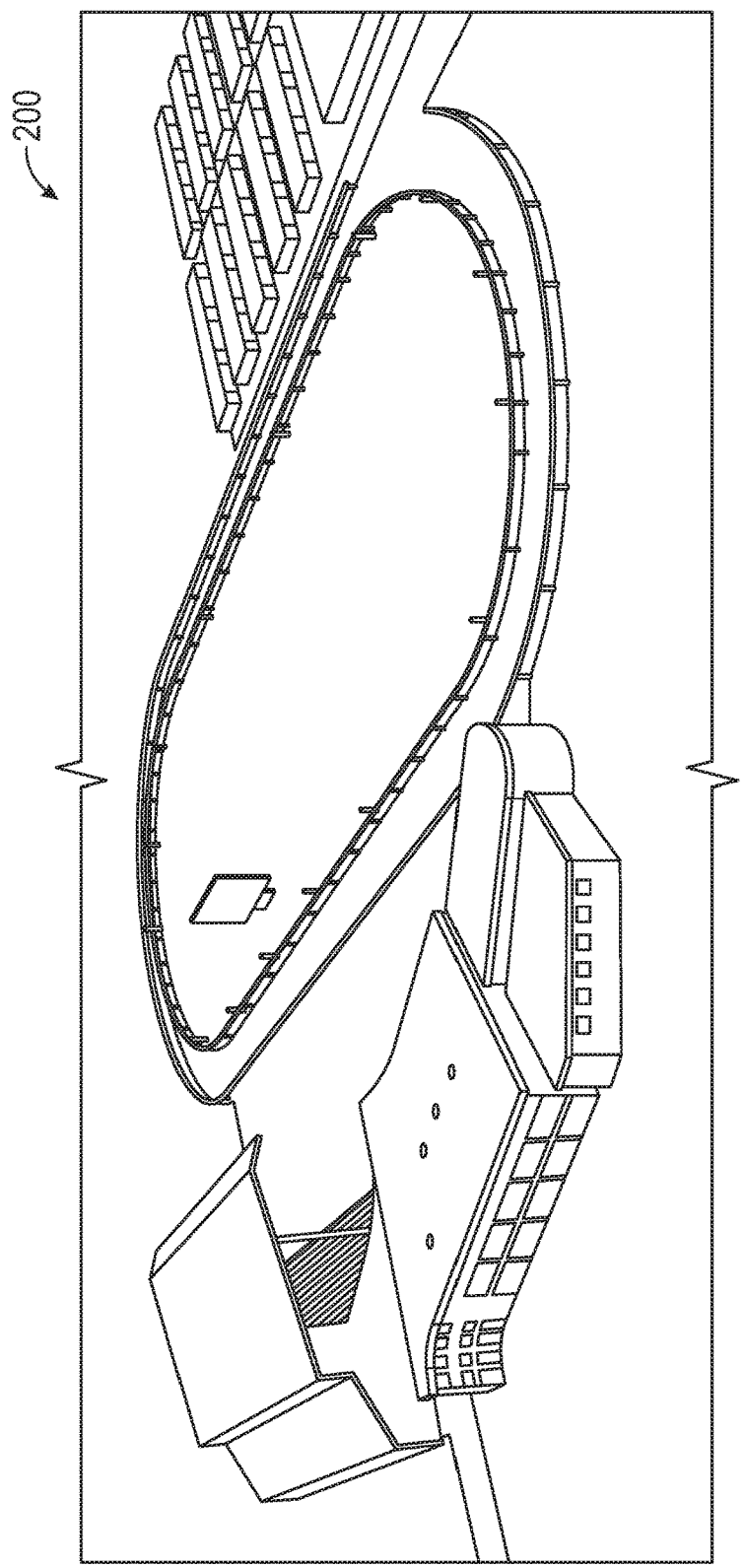
FIG. 2A is an exemplary embodiment of a racetrack with associated stables.
Figure 2B:
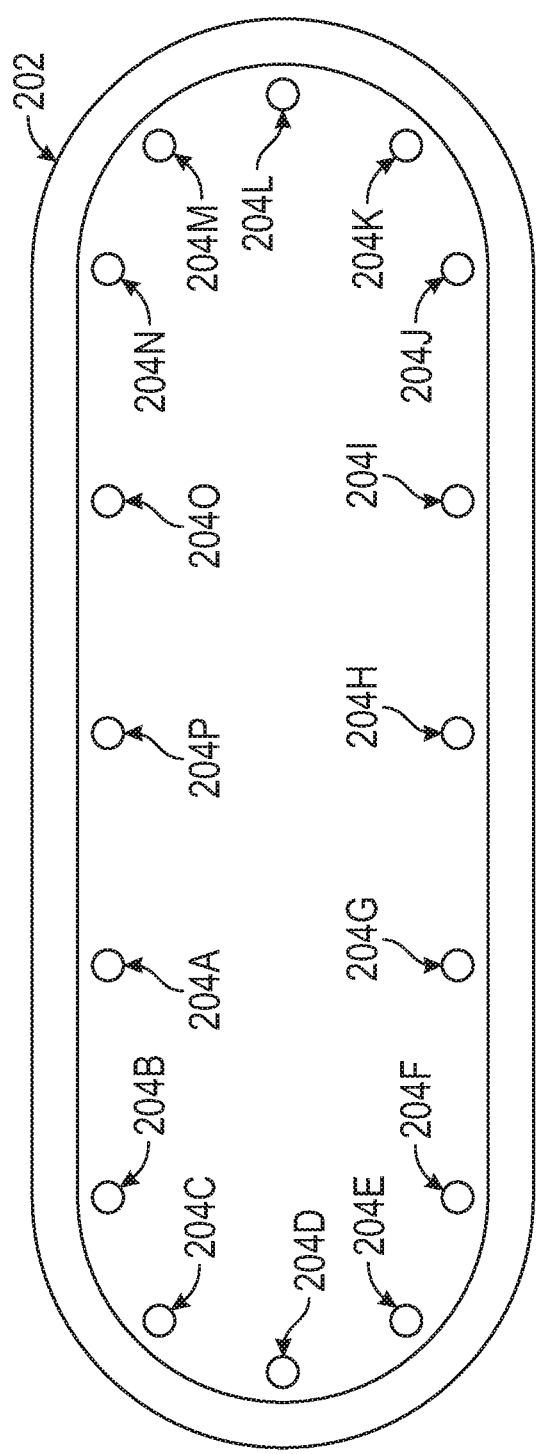
FIG. 2B is an exemplary embodiment of the layout of the racetrack from FIG. 2A.
Figure 3:
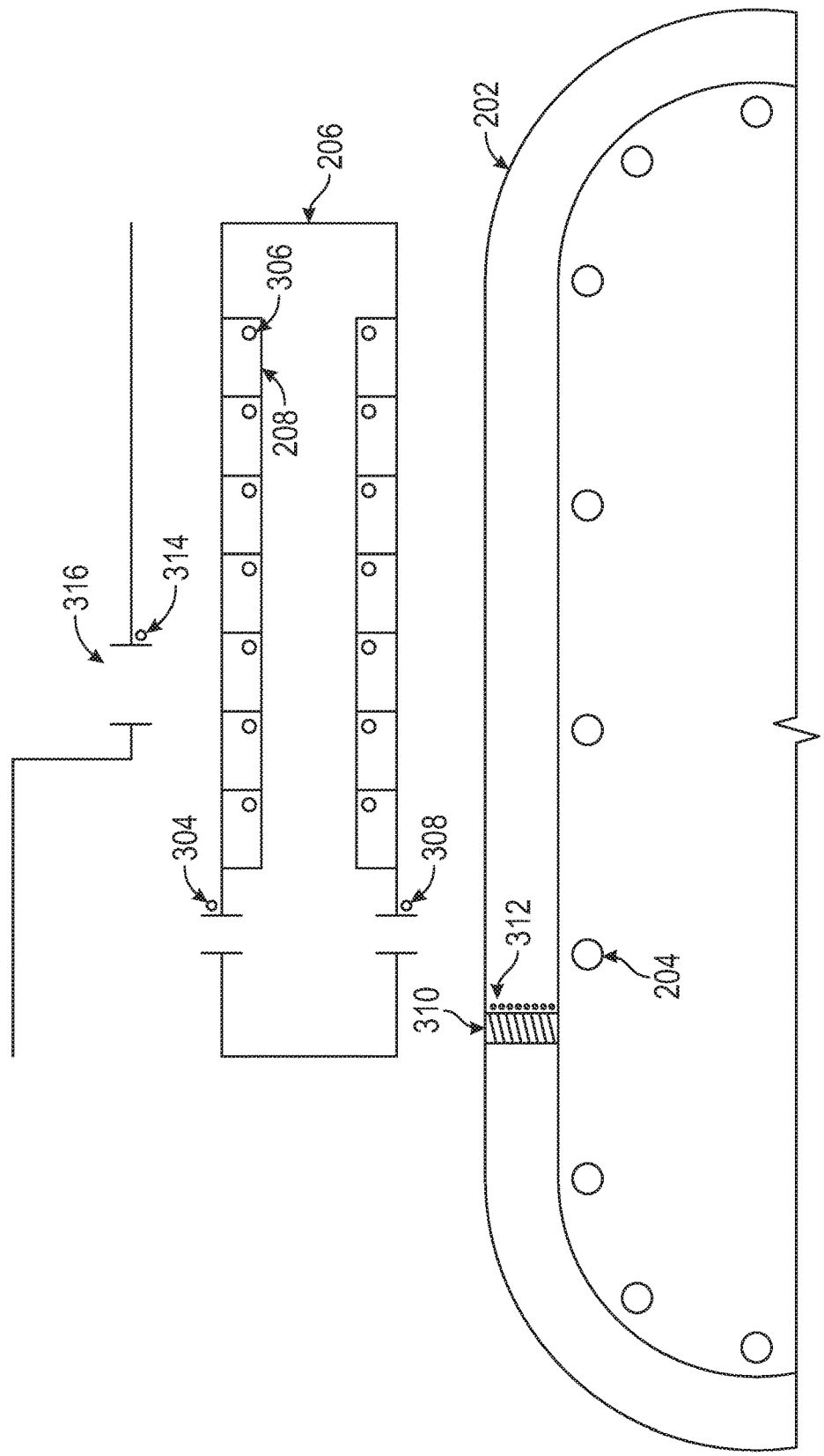
FIG. 3 is an exemplary embodiment of the arrangement of track readers at various locations at a race ground.

Racing animals are frequently at race grounds 200 like the exemplary racetrack 202 in FIG. 2A. There are many times when a horse's 102 location at the race grounds 200 needs to be determined. FIG. 3 also show readers at various "checkpoints" throughout the facility. This includes when they enter or exit the grounds through an entrance 316, when they enter and exit the stables 206, when the enter the racetrack 202. A horse's 102 location at specific points on the racetrack 202 is also needed, and may be determined by any means known to those skilled in the art.

In an exemplary embodiment, the tag 100 may give off a signal 108 that may be detectable by a reader 106 at a fixed location. Examples of fixed locations where a reader 106 may be located include the entrance 316 to the race grounds 200, doorways into a stable 206, doorways into an individual stall 208, entrances into the racetrack 202, and entrances into the gate 310 in preparation for the race. With a series of readers 106, the general location of horse 102 may be known at any time. This would allow users to know if all the horses 102 are present for a race and to verify which horses 102 are actually present in the race grounds 200. This also provides a level of security to know when an unauthorized horse 102 has entered or left a race grounds 200. Readers 106 maybe portable as well. The readers 106 may relay information to a secondary location as needed, such as a security station.

Figure 6A:
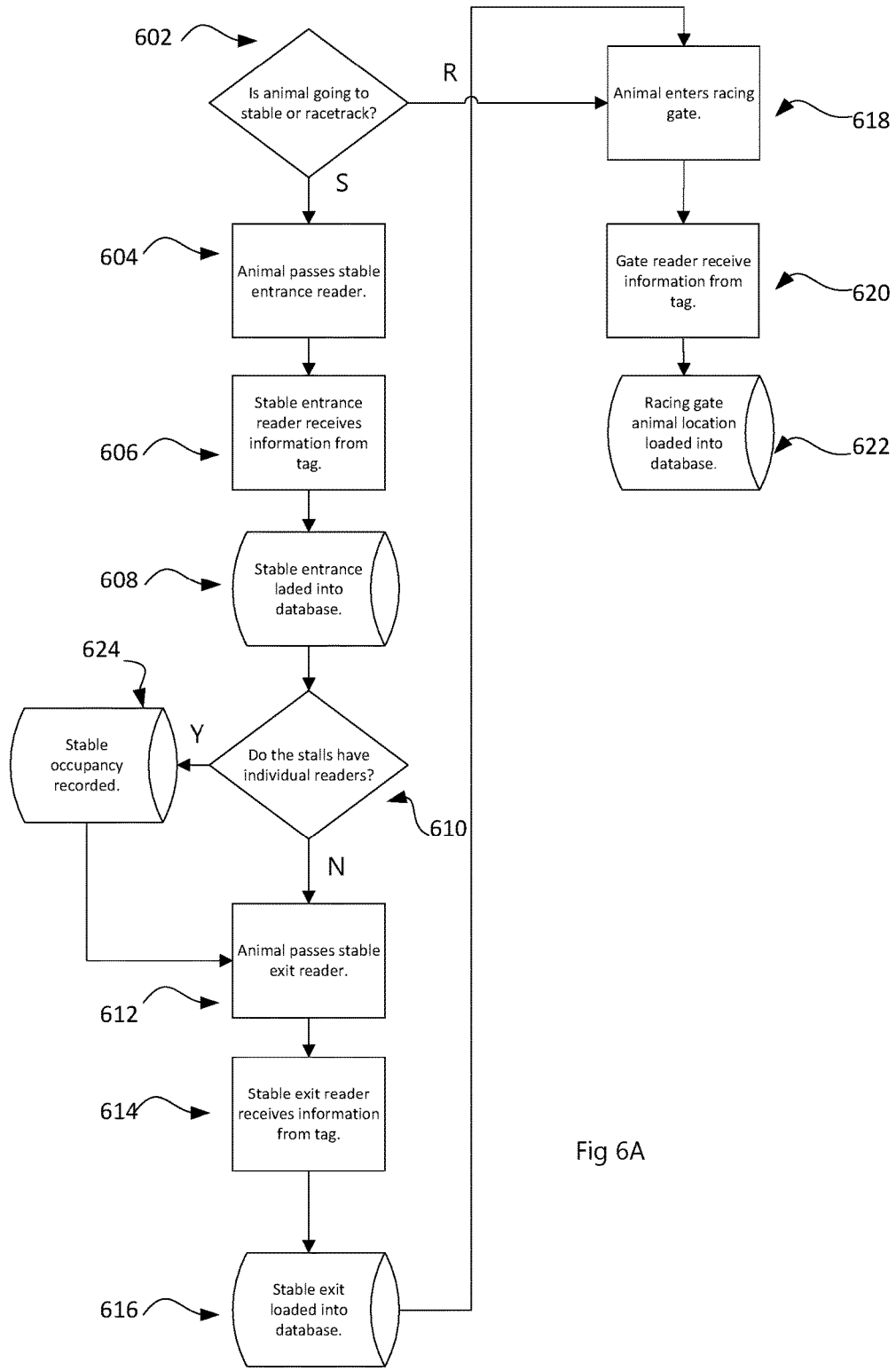
FIG. 6A is a flowchart of an exemplary embodiment showing the process of tagged animals entering the racing post.

FIG. 3 shows how there are readers 106 at the various locations around the race grounds 200. The horse 102 is initially admitted at the entrance 316, where it is interrogated by the entrance reader 314, where documentation may be taken as described below. An example of recording the location of a horse 102 at the race grounds 200 up until race time is shown in FIG. 6A. The question would be if the horse 102 is going into the racetrack 202 or to the stable 206 (step 602). If the horse 102 is going into the stable 206, then the horse 102 passes the first stable reader 304 (step 604) and receives information from the tag 100 (step 606). The entrance is recorded into the database (step 608). The horse 102 may stay in a common area or be placed in a stall 208. If the horse 102 then goes to an individual stall 208, and if the stall 208 has a stall reader 306 (step 610), then the location of the horse 102 is recorded once it enters the stall 208 (step 624). When the horse 102 leaves the stable 206, it will pass the second stable reader 308 (step 612) and record the horse 102 has left the stable 206 (step 614) and update the database (step 616). The horse 102 enters the gate 310 (step 618), where a gate reader 312 is available for each chute. Once the horse 102 enters the gate 310, the gate reader 312 receives the information (step 620) and updates the database (step 622). If the horse 102 is not going to the stable 206 (step 602), then the horse 102 goes directly to the gate 310 (step 618) as continues as previously described. Methods for monitoring the horse's 120 location in the area using these readers 106 do not depart form the scope of the invention.

Another exemplary embodiment would use racetrack readers 204 at predetermined intervals along the racetrack 202. As horses 102 with the tags 100 pass a racetrack reader 204, their location is recorded along with their arrival time. When said tags 100 and racetrack readers 204 have sufficient precision to differentiate between the position of the tag 100 in each horse 102, they would be able to definitely determine the winner of a race.

Figure 6B:
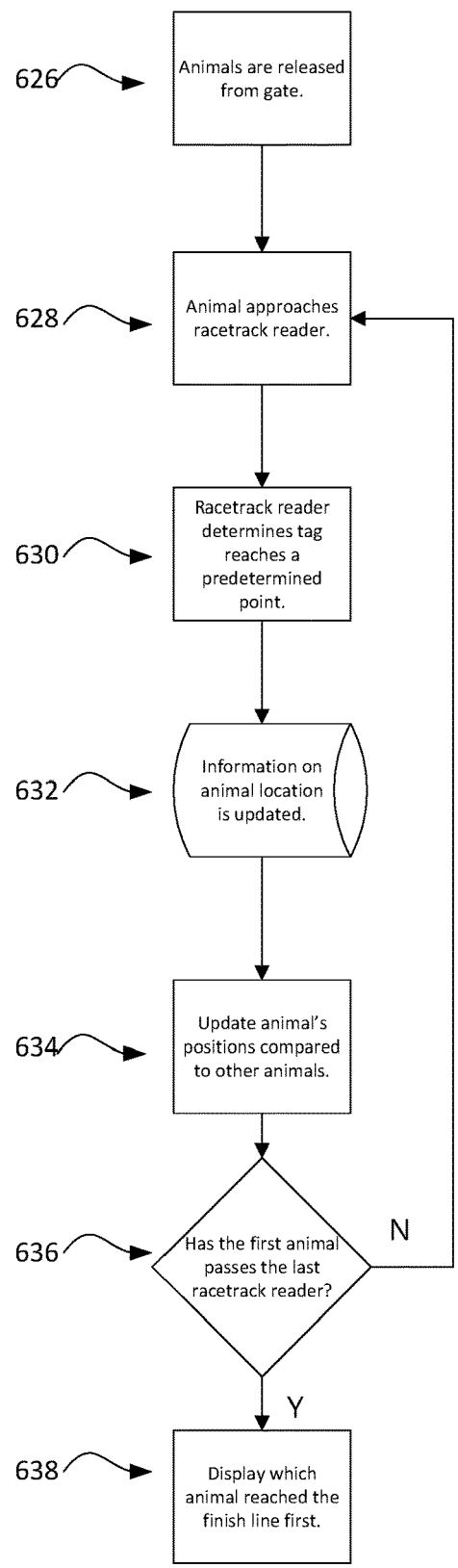
FIG. 6B is a flowchart of an exemplary embodiment showing how racing results are determined.

FIG. 6B shows how the racetrack readers 204 would work in an exemplary embodiment to determine the placing of a horse 102 in a race. The horses 102 are released from the gate 310 (step 626). The horses 102 approach the first racetrack reader 204a (step 628). The racetrack reader 204a determines when the horse 102 reaches the plane of the first racetrack reader 204a (step 630). The system then records when each horse 102 reached the first racetrack reader 204a (step 632), and the position of the horses 102 are updated determine which horses 102 are in which position (step 634). If the first horse 102 has not passed the last racetrack reader (step 636), the process is repeated for each racetrack reader 204. Once the first horse 102 passes the last racetrack reader 204p (step 636), the system determines which horse 102 passed first to declare the winner (step 638).

In a further alternative embodiment, the racetrack readers 204 may be placed on a linear racetrack. In this embodiment, the racetrack reader 204 would function in a manner similar to the previous racetrack 202. As a horse 102 approaches each racetrack reader 204 is approached, the position of the tag 100 is recorded.

In an exemplary embodiment, the location of the tag 100 may be determined by analyzing the signal 108 transmitted by the tag 100. If the tag 100 is in an active embodiment or passive and receiving power and/or an interrogation signal 110 from a reader 106, the signal 108 will broadcast, then a reader 106 would indicate that the tag 100 is in a known proximity to the reader 106. When the horse 102 is away from a reader 106, either the tag 100 will stop transmitting due to a loss of power and or interrogation signal 110 in a passive configuration or the reader 106 will not detect it due to the tag 100 being out of range in an active configuration.

If the tag 100 is active in a racing configuration, then the racetrack readers 204 would be able to determine the time the horse 102 was at the location of the racetrack reader 204 by any means known to those skilled in the art. For example, the reader could identify a signal 108 and determine when the signal 108 was strongest. By detecting when the signal 108 was strongest, the racetrack reader 204 can determine when the horse 102 ran by. If the tag 100 is passive, then the racetrack readers 204 may send an interrogation signal 110 (an possibly wireless power) to activate the tag 100 to broadcast a signal 108. The same principles of determining when the signal 108 was strongest to determine when the horse 102 passed the racetrack reader 204. In these exemplary embodiments, the signal does not contain location information. The location is determined by the reader 106. Any other means known using a signal 108 that does not contain location information may be used without departing form the scope of the invention In an alternative embodiment, the location of the tag 100 may be determined by use of a known radio navigation system that places location information into the signal 108. In an exemplary embodiment, Global Positioning System (GPS) will be used. The tag 100 determines its location and transmits the information to a reader 106 in the signal 108. This GPS enabled tag 100 may be powered by any means known to those skilled in the art, including an internal power supply or by an external magnetic field. GPS enabled tags 100 have the additional advantage of giving a more precise location rather than indication of proximity to a fixed location, such as a racetrack reader 204. The horse's 102 progress would be tracked by comparing the GPS location against the known information on the racetrack 202 to determine which horse 102 was in which position. When the reader 106 receives a location from a GPS enabled tag 100, it can record a precise location that would be able to provide a location within the accuracy and precision of the tag 100. Any other mechanism of placing the location information in the signal 108 may be used without departing from the scope of the invention.

Figure 4:
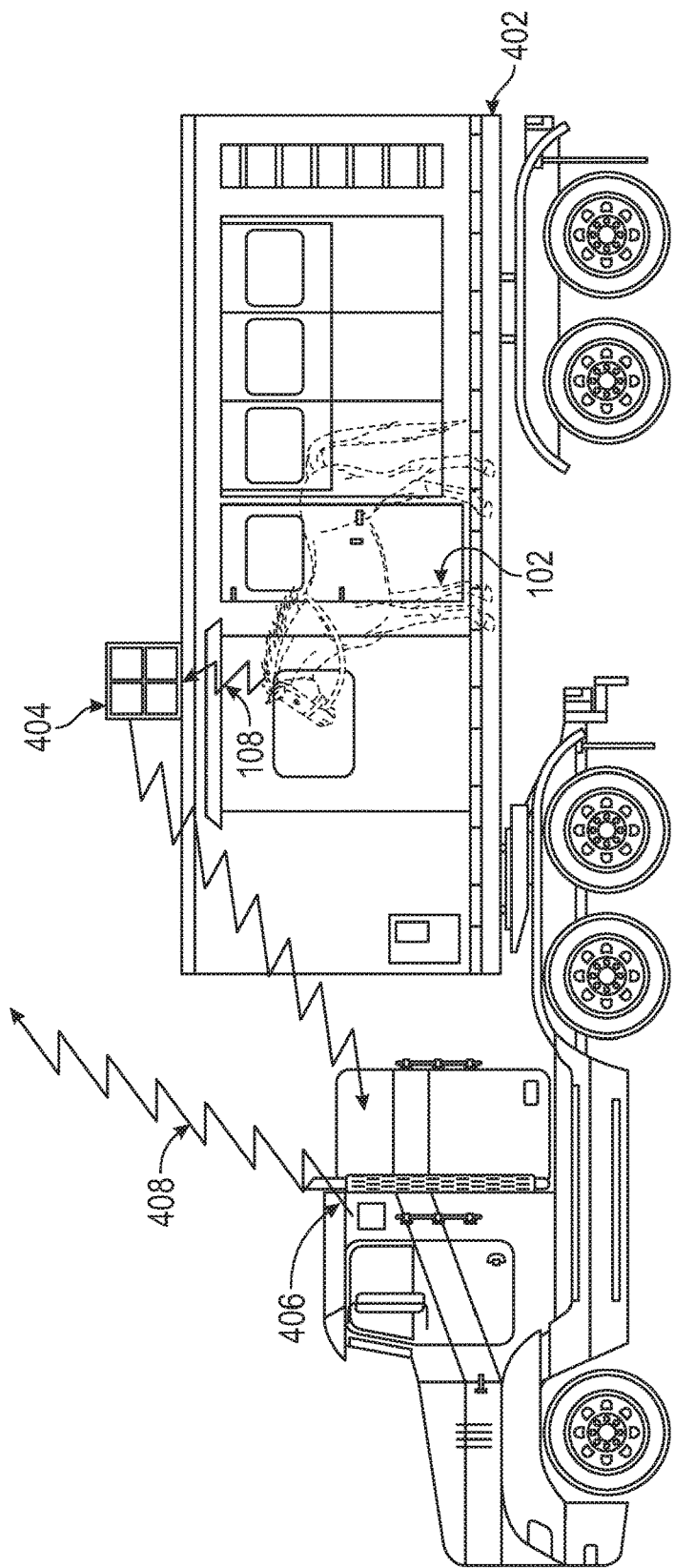
FIG. 4 is an alternative exemplary embodiment of how readers may transmit from a location remotely.

Hybrid location systems such as those shown in FIG. 4 are also available to track a horse 102. In one example, a tag 100 interacts with a vehicle mounted reader 404, such as one installed in a horse trailer 402. The tag 100 would emit a signal 108 to a vehicle mounted reader 404 in the horse trailer 402. The horse trailer 402 would have a GPS system that could relay the location to a remote party. This may be relayed by any means know to those skilled in the art, such as a cell phone 406. In an exemplary embodiment, the driver of the horse trailer 402 may "pair" his phone with the vehicle mounted reader 404. The tag 100 indicates the horse 102 is in the horse trailer 402 or has left the trailer and is nearby. The vehicle mounted reader 404 calculates the locations of the horse trailer 402, which is then communicated with the cell phone. The cell phone then relays the locations over a data link 408, allowing remote parties to know the location of the horse 102. Any combination of these elements may be combined without departing form the scope of the invention.

As an additional feature of an exemplary embodiment of the system alerts the user if horse 102 has left an area, deviated from a predetermined route, or been stationary for a given length of time. Further additional embodiments could also send information such as the horse temperature or other medical information.

An optional additional feature of the tags 100 includes a recordkeeping function. In a basic format, the tag 100 keeps a unique identification number correlated to the horse 102. In an alternative embodiment, the tag 100 might transmit a hyperlink that the reader 106 can use to access a history of the horse 102. In a further additional embodiment, the tag 100 may contain memory (either fixed or rewritable) that contains information that is needed to properly document the horse 102. This may include information such as breeding information, records of vaccinations, or other information required by the various horse associations. These records could also be loaded into a master database to advise owners when a horse 102 is due for vaccinations or related medical issues.

Figure 7A:
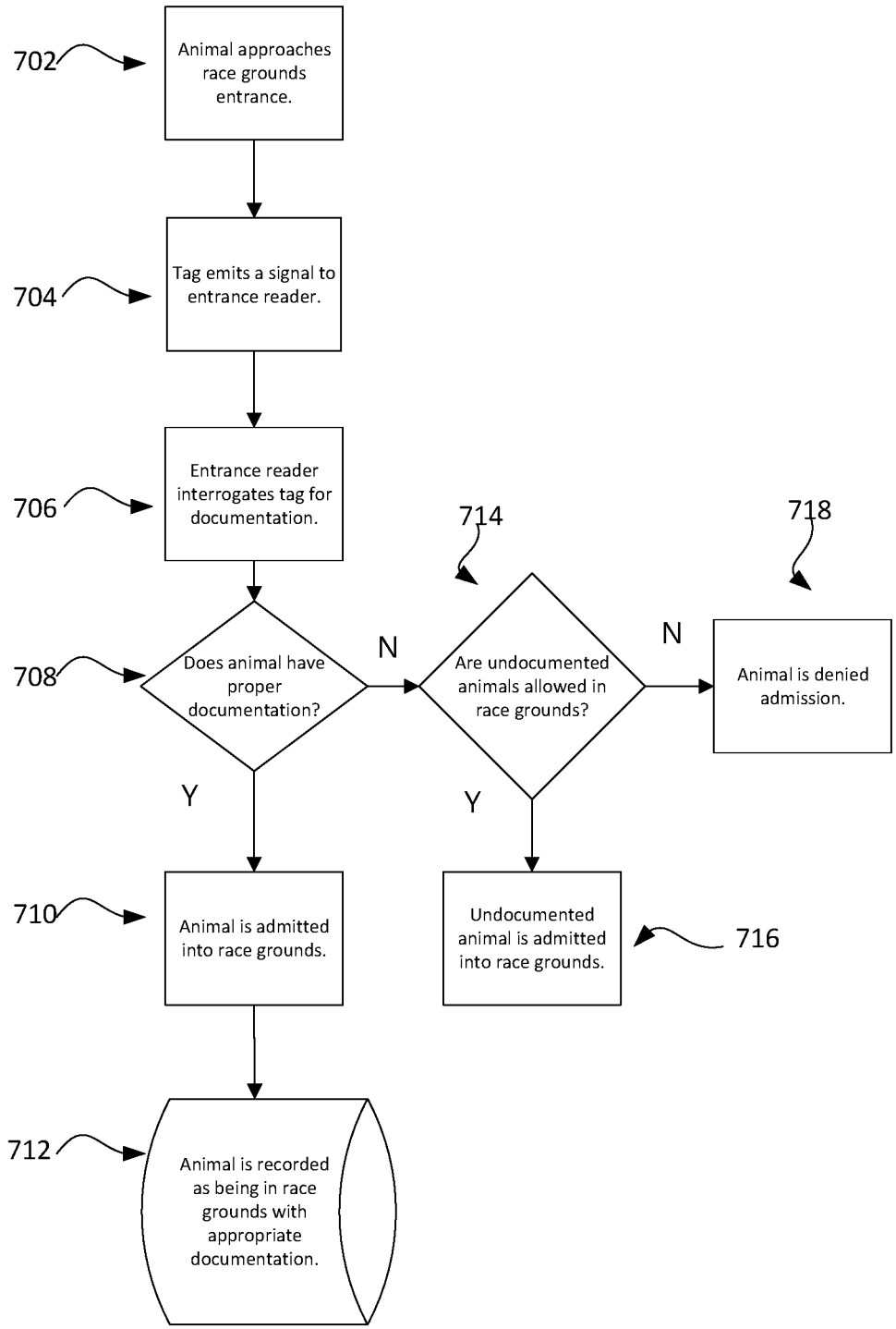
FIG. 7A is a flowchart of an exemplary embodiment showing the process of tagged animals being admitted into the race grounds.

The interrogation of the horse's 102 record for initial entry into the race grounds 200 may follow an exemplary embodiment as shown in FIG. 7A. As the horse 102 approaches the race grounds 200 (step 702), the tag 100 emits a signal 108 to the entrance reader 314 (step 704). The entrance reader 314 then sends a signal to retrieve information from the tag 100 (step 706). If the tag 100 contains proper documentation (step 708), then the horse 102 is admitted (step 710). The proper documentation is loaded into the database (step 712). If the tag 100 does not contain the documentation (step 708), the system looks to see if undocumented horses 102 are allowed inside (step 714). If they are, then the undocumented horse 102 is allowed into the race grounds 200 (step 716). If undocumented horses 102 are not allowed inside (step 714), then the horse 102 is denied admission (step 718).

Figure 7B:
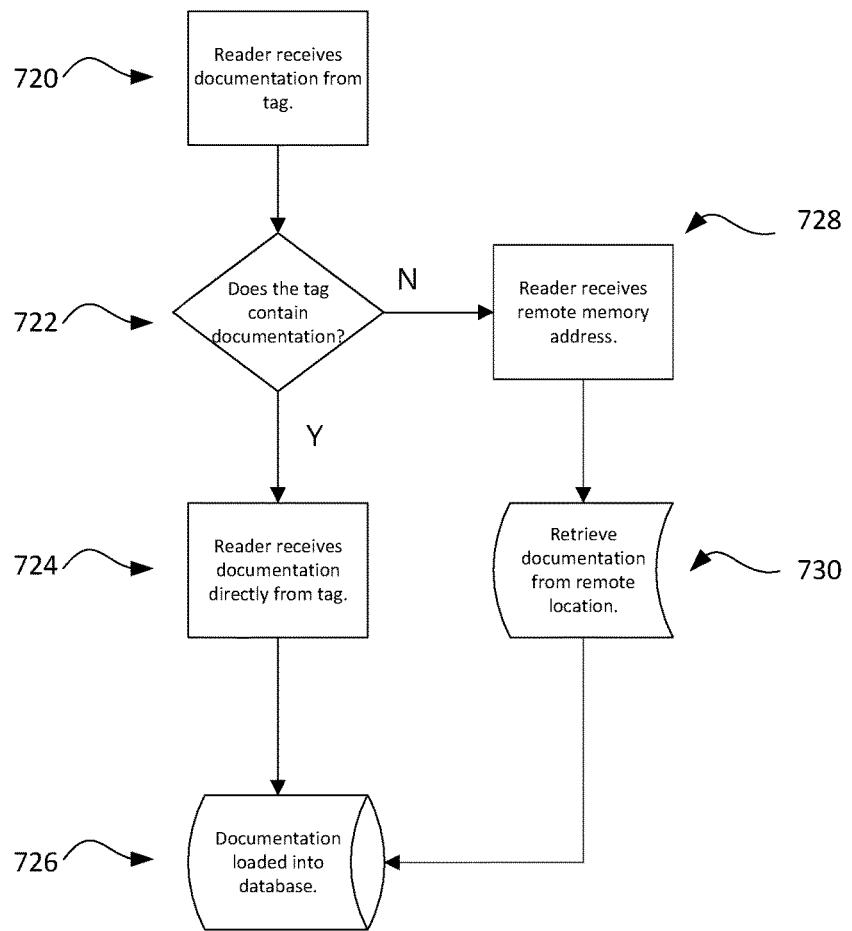
FIG. 7B is a flowchart of an exemplary embodiment showing the process of interrogating the tag to receive information.

When any reader 106 is reading the tag 100 for documentation (step 720), the reader 106 will look to see if the information is on the tag 100 or remotely stored (step 722) as shown in FIG. 7B. If the tag 100 contains documentation (step 722), then the reader 106 receives the information from the tag 100 (step 724) and updates the database (step 726). If the tag 100 does not contain the documentation (step 722), the reader 106 looks to see if there is a hyperlink where the information is recorded (step 728). If so, the information is retrieved form the remote location and received by the reader 106 (step 730). The information in then loaded into the local database (step 726).

Figure 7C:
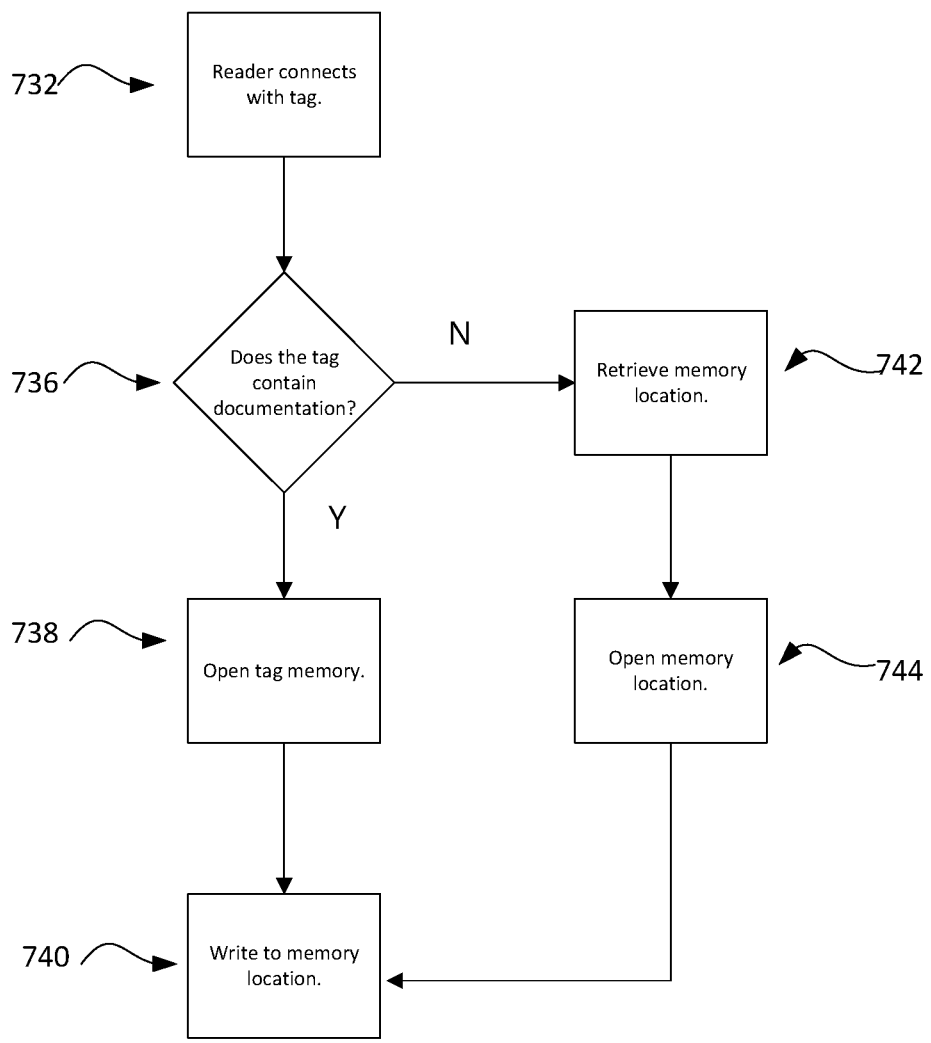
FIG. 7C is a flowchart of an exemplary embodiment showing how information is recorded.

As shown in FIG. 7C, while the reader 106 can receive this documentation, the reader 106 may also be configured to record into the memory in the tag 100. For example, if the horse 102 has been inoculated for a disease, the tag 100 could contain the information to be retrieved later. If the hyperlink method to record is used, the reader 106 could also be used to upload information to the remote location. The process begins by the reader 106 connecting to the tag 100 (step 732). Once the reader 106 connects with the tag 100, the reader 106 would check to see if the information is recorded on the tag 100 or recorded remotely (step 736). If the information is recorded on the tag 100, then the tag's 100 memory is opened (step 738), and information is recorded (step 740). If the information is recorded remotely (step 736), then that memory address is retrieved (step 742) and is opened (step 744). The information is then recorded in the memory address (step 740).

In an additional exemplary embodiment, the tag 100 may also provide diagnostic functions for the horse 102. Sensors can be installed in the tag 100 to detect heart rate, blood pressure, respiration, and other medial data that may be related to the reader 106.

The reader 106 in an exemplary embodiment may be a general purpose computer, such as that on a cell phone, or can be a dedicated reader 106. In an exemplary embodiment, the tag 100 receives power from a power supply 114 on the bridle 112. The tag 100 determines the coordinates of the tag 100 and relays the information by signal 108 to a cell phone via a wireless connections. This information may be communicated to a remote system via cell phone data link 408. This allows a cell phone and a tag 100 to provide updates on a horse's 102 location.

Multiple configurations are possible without departing form the scope of this invention. For example, the tag 100 and the power source may be an integrated unit. Additionally, the reader 106 and communications device might also be integrated. Steps in the method may also be combined without departing from the scope of the invention.

One of skill in the art will appreciate that embodiments provide improved ability to track the location of animals with particular benefit in competitive environments. Although specific embodiments are illustrated and described herein, it will be appreciated by those of ordinary skill in the art that any arrangement which is calculated to achieve the same purpose can be substituted for the specific embodiments shown. This specification is intended to cover any adaptations or variations of embodiments. In particular, one of skill in the art will appreciate that the names and terminology are not intended to limit embodiments. Furthermore, additional apparatus can be added to the components, functions can be rearranged among components, and new components corresponding to future enhancements and future physical devices used in embodiments can be introduced without departing from the scope of the invention. The terminology used in this application is intended to include all embodiments and alternatives which provide the same functionality as described herein.

The invention claimed is:

1. A method for collecting and transmitting information from an animal, comprising:
    a. Implanting a tag in a lip of said animal; and
    b. Receiving a signal to determine location of said animal.
2. The method of claim 1, further comprising:
    a. Comparing said location of said animal to a known position; and
    b. Determining when said animal has reached said known position.
3. The method of claim 1, wherein determining said location is based on a comparing said signal to a known reference.
4. The method of claim 1, wherein said signal contains location information for said tag.
5. The method of claim 1, wherein said tag contains memory.
6. The method of claim 5, wherein said memory contains information that may be accessed from an external device.
7. The method of claim 5, wherein said memory contains a hyperlink to a remote memory location that contains information that may be accessed from an external device.
8. The method of claim 1, further comprising:
    a. Receiving a second signal from a second tag from a second animal; and
    b. Determining which of said animal or said second animal reached a location first.
9. A system for collecting and transmitting information on an animal, comprising:
    a. At least one tag implanted in a lip of at least one animal; and
    b. A reader capable of receiving information from said at least one tag.
10. The system of claim 9, wherein said at least one tag transmits information to said reader.
11. The system of claim 9, wherein said at least one tag comprises memory.
12. The system of claim 11, wherein said reader is capable of recording information in said memory.
13. The system of claim 9, wherein said at least one tag communicates with a reader with a known location to determine the location of said at least one animal.
14. The system of claim 9, wherein said at least one tag contains a geolocation system capable of transmitting a location to said reader.
15. The system of claim 9, further comprising:
    a. A second at least one tag implanted in the lip of a second at least one animal;
    b. Wherein said reader can determine when said at least one tag and said second at least one tag reach a predetermined location; and
    c. Wherein said reader can determine which of said at least one tag and said second at least one tag arrived at said predetermined location first.

* * * * *